US010307354B2

(12) United States Patent
Gebert-Schwarzwaelder et al.

(10) Patent No.: US 10,307,354 B2
(45) Date of Patent: Jun. 4, 2019

(54) RESORCINOL DERIVATIVES IN COMPOSITIONS FOR SIMULTANEOUS RESHAPING AND COLORING OF KERATINOUS FIBERS

(71) Applicant: Henkel AG & Co. KGaA, Duesseldorf (DE)

(72) Inventors: Antje Gebert-Schwarzwaelder, Neuss (DE); Annika Koenen, Grevenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 17 days.

(21) Appl. No.: 15/539,232

(22) PCT Filed: Nov. 17, 2015

(86) PCT No.: PCT/EP2015/076790
§ 371 (c)(1),
(2) Date: Jun. 23, 2017

(87) PCT Pub. No.: WO2016/096283
PCT Pub. Date: Jun. 23, 2016

(65) Prior Publication Data
US 2018/0177697 A1 Jun. 28, 2018

(30) Foreign Application Priority Data

Dec. 17, 2014 (DE) .......................... 10 2014 226 320

(51) Int. Cl.
*A61Q 5/10* (2006.01)
*A61K 8/34* (2006.01)
*A61Q 5/04* (2006.01)
*A61Q 5/06* (2006.01)
*A61K 8/22* (2006.01)
*A61K 8/46* (2006.01)

(52) U.S. Cl.
CPC ................ *A61K 8/347* (2013.01); *A61K 8/22* (2013.01); *A61K 8/463* (2013.01); *A61Q 5/04* (2013.01); *A61Q 5/06* (2013.01); *A61Q 5/10* (2013.01); *A61K 2800/4324* (2013.01); *A61K 2800/87* (2013.01); *A61K 2800/882* (2013.01)

(58) Field of Classification Search
CPC ... A61Q 5/10; A61Q 5/04; A61Q 5/06; A61K 8/347; A61K 8/22; A61K 8/463; A61K 2800/882; A61K 2800/87; A61K 2800/4324

See application file for complete search history.

(56) References Cited

U.S. PATENT DOCUMENTS

| 5,196,189 A | 3/1993 | Jacquet et al. |
| 2003/0084518 A1 | 5/2003 | Schonert et al. |
| 2003/0188392 A1* | 10/2003 | Laurent ................. A61K 8/411 8/406 |
| 2012/0312318 A1 | 12/2012 | Krippahl et al. |
| 2014/0245541 A1* | 9/2014 | Gross ..................... A61K 8/416 8/406 |

FOREIGN PATENT DOCUMENTS

| DE | 19713698 C1 | 6/1998 |
| DE | 102005061023 A1 | 6/2007 |
| EP | 0310675 A1 | 4/1989 |
| EP | 0352375 A1 | 1/1990 |
| EP | 1743620 A1 | 1/2007 |
| WO | 2012038114 A2 | 3/2012 |

OTHER PUBLICATIONS

Wong, Michael et al., "Mechanism of Hair Straightening", J. Soc. Cosmet. Chem., 45, Nov./Dec. 1994, pp. 347-352.
EPO, International Search Report and Written Opinion issued in International Application No. PCT/EP2015/076790, dated Mar. 16, 2016.

* cited by examiner

*Primary Examiner* — Eisa B Elhilo
(74) *Attorney, Agent, or Firm* — Lorenz & Kopf, LLP

(57) ABSTRACT

The present disclosure concerns a multi-component packing unit (kit of parts) for reshaping and coloring keratinous fibers, more particularly human hair, comprising at least two separately packaged preparations (A) and (B), the first preparation (A) comprising, in a cosmetic vehicle (A1), one or more resorcinol derivatives from the group consisting of resorcinol, 2-methylresorcinol and 4-chlororesorcinol, and (A2) one or more oxidation dye precursors from the group consisting of p-phenylenediamines, p-aminophenols, 2,4,5,6-tetraaminopyrimidines and 4,5-diaminopyrazoles, and the second preparation (B) comprising, in a cosmetic vehicle (B1), hydrogen peroxide, wherein the molar ratio of all resorcinol derivatives (A1) in the preparation (A) to all developer-type oxidation dyes (A2) in the preparation (A), i.e. the molar ratio (A1)/(A2), is at least about 1.2.

16 Claims, No Drawings

RESORCINOL DERIVATIVES IN COMPOSITIONS FOR SIMULTANEOUS RESHAPING AND COLORING OF KERATINOUS FIBERS

CROSS-REFERENCE TO RELATED APPLICATION

This application is a U.S. National-Stage entry under 35 U.S.C. § 371 based on International Application No. PCT/EP2015/076790, filed Nov. 17, 2015, which was published under PCT Article 21(2) and which claims priority to German Application No. 10 2014 226 320.4, filed Dec. 17, 2014, which are all hereby incorporated in their entirety by reference.

TECHNICAL FIELD

The present disclosure falls within the field of cosmetics and relates to multicomponent packaging units for the simultaneous reshaping and coloring of keratinous fibers, in particular human hair, which comprise at least two separately packaged preparations (A) and (B). The first preparation (A) comprises one or more resorcinol derivatives and developer-type oxidation dye precursors and is characterized by a molar excess of resorcinol derivatives. The second preparation (B) comprises hydrogen peroxide. A second subject of the present disclosure is a method for the simultaneous reshaping and coloring of keratinic fibers, in which the preparations of the aforementioned multicomponent packaging unit are used. A third subject of the present disclosure is the use of resorcinol and derivatives thereof in oxidative dyeing agents for the reshaping of human hair.

BACKGROUND

The user resorts to cosmetic reshaping agents to produce curls or to straighten the hair. A long-lasting reshaping of keratinic fibers is normally carried out in such a way that the fibers are mechanically shaped and the shape is set using suitable aids. The fibers are treated with a keratin-reducing preparation before, during, or after this shaping. After a rinsing process, the fiber is then treated in the so-called fixing step with an oxidizing agent preparation, rinsed, and after or during the fixing step freed of shaping aids (e.g., curlers, rollers). If a mercaptan, e.g., ammonium thioglycolate, is used as the keratin-reducing component, part of the disulfide bridges of the keratin molecule is cleaved to —SH groups, resulting in a softening of the keratin fibers. During the later oxidative fixation, disulfide bridges are again formed in the hair keratin, so that the keratin structure is fixed in the given shape. Alternatively, it is known to use sulfite in place of mercaptans for hair shaping. The disulfide bridges of keratin are cleaved by hydrogen sulfite solutions and/or sulfite solutions and/or disulfite solutions in a sulfitolysis according to the equation

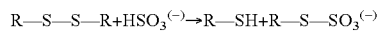

$$R-S-S-R+HSO_3^{(-)} \rightarrow R-SH+R-S-SO_3^{(-)}$$

and softening of the keratin fibers is achieved in this way. Reducing agents comprising hydrogen sulfite, sulfite, or disulfite do not have the strong characteristic odor of mercaptan-containing agents. The cleavage can be reversed as previously described in a fixing step with the aid of an oxidizing agent with the formation of new disulfide bridges.

The permanent straightening of keratin-containing fibers is achieved similarly by the use of keratin-reducing and keratin-oxidizing compositions. In a suitable method, the curly hair is either wound on curlers with a large diameter of normally more than 15 mm or the hair is combed smooth under the effect of the keratin-reducing composition. Instead of using curlers, it is also possible to straighten the fiber on a straightening board or to straighten the hair by pulling with a comb during the straightening process. Straightening boards are usually rectangular panels, e.g., made of plastic. In so doing, the fiber is preferably wetted with the keratin-reducing preparation.

Another option for straightening hair is straightening with use of a straightening iron after prior application of alkaline products. Such alkaline reshaping agents, in contrast to reshaping with use of keratin-reducing and keratin-oxidizing compositions, do not lead to a conversion of the disulfide bridges, but to a destruction of the disulfide bridges with the formation of monosulfide bridges. Depending on the concentration and application time of the alkaline reshaping agents, protein chains are also cleaved hydrolytically. The pH value of the alkaline reshaping agents is typically in the range of 1-14, preferably of 12-13.

So-called oxidation dyes are used to achieve permanent, intense colors with good fastness properties. Such dyes customarily contain oxidation dye precursors, so-called developer components and coupler components. The developer components form the actual dyes under the influence of oxidizing agents during coupling with one or more coupler components. The oxidation dyes are characterized by intense, excellent, long-lasting coloring results.

If the user desires both a permanent reshaping and coloring of hair, thus the previously described reshaping and coloring methods can be combined. Suitable methods for the simultaneous reshaping and coloring of keratinic fibers have already been described in the literature. Thus, DE 197 13 698 C1 discloses a method in which an oxidation dye precursor and/or a direct dye are added to the oxidizing agent for fixing reshaped hair.

Methods for the simultaneous reshaping and coloring of hair, in which a keratin-reducing preparation is used which already comprises the necessary dyes and/or dye precursors, are known from EP 352 375 A1, EP 1 287 812 A2, and DE 10 2005 061 023 A1.

All these methods known from the prior art are based on the use of a reducing agent and a subsequent fixation by an oxidizing agent, wherein dyes (or dye precursors) are added to either the reducing agent component or, however, to the subsequent used oxidizing agent component.

The reduction of the disulfide bridges in the keratin material, which occurs during the reshaping, is in fact the prerequisite for achieving a satisfactory reshaping effect, but simultaneously also involves the risk of massive hair damage. The cysteine units with disulfide bonds essential for the physical stability of the hair are first cleaved reductively to cysteine, but cannot be restored completely during the subsequent fixation, because part of the cysteine converts to cysteine oxides or cysteic acid in secondary reactions. The hair brought into the malleable state during reshaping thus hardens again by the oxidative fixation and does not resume the original chemical or physical state, however.

After the reshaping treatment, curled, or alternatively straightened, hair results, which is under tension internally, is not in a stable state thermodynamically, comprises new amino acids (such as cysteine oxides and cysteic acid), and is incompletely crosslinked. The user perceives this state as more or less highly pronounced hair damage, which is a general disadvantage of all these reshaping methods, because the use of reducing agents cannot be avoided due to the process.

BRIEF SUMMARY

Multicomponent packaging units for reshaping and coloring keratinic fibers and associated methods are provided herein. In an exemplary embodiment, a multicomponent packaging unit for reshaping and coloring keratinic fibers includes at least two separately packaged preparations (A) and (B). The first preparation (A) contains, in a cosmetic carrier, (A1) one or more resorcinol derivatives from the group including resorcinol, 2-methylresorcinol, and 4-chlororesorcinol, and (A2) one or more oxidation dye precursors from the group including p-phenylenediamines, p-aminophenols, 2,4,5,6-tetraaminopyrimidines, 4,5-diaminopyrazoles, and/or the physiologically acceptable salts thereof. The second preparation (B) contains, in a cosmetic carrier, (B1) hydrogen peroxide. The molar ratio of all resorcinol derivatives (A1), contained in preparation (A), to all developer-type oxidation dyes (A2), contained in preparation (A) define the molar ratio (A1)/(A2) having a value of at least about 1.2.

In another exemplary embodiment, a method for reshaping and coloring human hair includes preparing a ready-to-use reshaping and coloring agent by mixing a preparation (A) with a preparation (B). The ready-to-use reshaping and coloring agent is applied to the hair. The hair is mechanically reshaped, rinsed, and optionally dried.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was now the object of the present disclosure to provide a reshaping and coloring method for keratin-containing fibers, in particular for human hair, which delivers a very good and long-lasting reshaping and coloring result, but in so doing does not damage the fiber and preserves the structure of the fiber.

If the previously described reshaping and coloring methods are combined or carried out successively immediately one after the other, thus apart from the hair damage, the problem also arises of the interaction of both methods, which can lead to likewise unforeseeable as well as undesirable coloring results. Thus, for example, if the hair first is first colored and after this subjected to permanent waving or reductive straightening, the subsequent reduction process in the previously colored hair can lead to a breaking down of the artificial dyes. The consequence of this is a too low color intensity or, however, a color deviation from the desired shade. Furthermore, hair colored immediately beforehand reacts more rapidly to the permanent wave treatment, so that the degree of reshaping can be greater than desired and an overcurling results in the worst case.

On the other hand, it is also known that, if the hair is first treated with permanent wave or straightening agents and then colored, the hair becomes more absorptive due to the permanent wave or straightening agents and the dyes can therefore penetrate more rapidly into the hair fiber. The result is a too dark coloring result. In addition, the permanent waving or straightening can also be again lessened in an undesirable manner by the subsequent coloring.

A method for the simultaneous reshaping and coloring of the keratin fibers, which does not have these disadvantages, is thus not known from the prior art. A further object of the present disclosure therefore was to find agents for the simultaneous reshaping and coloring of keratinic fibers, in particular human hair, which enable both the reshaping and coloring but without both methods interacting in a disadvantageous manner, and without an unforeseeable reshaping and coloring result arising due to this interaction.

It is now known from the literature that hair can also be reshaped permanently by the use of swelling agents. A straightening effect is attributed to resorcinol in the article J Soc Cosmet. Chem (1994), 45, 347-352, but the article deals exclusively with the straightening of hair and coloring is not addressed at any point in this article.

During the work leading to present disclosure, it could now be found surprisingly that a simultaneous reshaping and oxidative coloring of keratinic fibers is possible, if the keratinic fibers are treated with a ready-to-use agent that comprises an oxidizing agent, developer-type oxidation dyes, and in addition a molar excess of resorcinol derivatives.

The resorcinol derivatives present in excess are hereby responsible both for straightening hair and also, together with the other oxidation dye precursors and the oxidizing agent, for coloring hair. It was possible in this way to reshape hair permanently and to color it simultaneously. An unforeseeable shift in shades of the coloring result or an unforeseeable lessening of the shaping result was not observed in this regard.

Moreover, additional reducing agent and strong alkalizing agents could be omitted with use of these agents, so that the fiber structure was less damaged and the keratin fibers were protected.

To avoid incompatibilities, the ready-to-use agent, which comprises the oxidizing agent, the developer-type oxidation dyes, and in addition certain resorcinol derivatives in a molar excess, is provided in the form of a multicomponent packaging unit (kit of parts), which comprises at least two separately packaged preparations (A) and (B), wherein preparation (A) comprises the oxidation dye precursors and resorcinol and preparation (B) comprises the oxidizing agent (hydrogen peroxide).

A first subject of the present disclosure is a multicomponent packaging unit (kit of parts) for reshaping and coloring keratinic fibers, in particular human hair, comprising at least two separately packaged preparations (A) and (B), wherein
the first preparation (A) comprises, in a cosmetic carrier,
 (A1) one or more resorcinol derivatives from the group comprising resorcinol, 2-methylresorcinol, and 4-chlororesorcinol, and
 (A2) one or more oxidation dye precursors from the group comprising p-phenylenediamines, p-aminophenols, 2,4,5,6-tetraaminopyrimidines, 4,5-diaminopyrazoles, and/or the physiologically acceptable salts thereof, and
the second preparation (B) comprises, in a cosmetic carrier, (B1) hydrogen peroxide,
wherein the molar ratio of all resorcinol derivatives (A1), contained in preparation (A), to all developer-type oxidation dyes (A2), contained in preparation (A), i.e., the molar ratio (A1)/(A2), has a value of at least about 1.2.

The term, used as contemplated herein, "reshaping of keratinic fibers," is understood to mean a permanent reshaping, which can be a wave or curling of the keratin fibers or also a straightening of the keratin fibers. Permanent reshapings are reshapings that are still present or visible also after at least one hair washing.

The term, "agents for coloring keratinic fibers," as used as contemplated herein is understood to mean oxidative dyes.

The coloring is produced by reacting developer-type oxidation dye precursors (A2) with the resorcinol derivatives acting as couplers under influence of the oxidizing agent, hydrogen peroxide. If other couplers are still present in addition, the coloring also occurs by reacting developer-type oxidation dye precursors (A2) with the additionally contained couplers. Depending on the amount of the employed oxidizing agent, the keratin fiber is lightened more or less greatly simultaneously during the coloring, because the oxidizing agent not only initiates the dye formation process of developers and couplers, but also breaks down oxidatively the hair's own pigments (melanins).

Keratinic fibers are understood to be wool, pelts, feathers, and particularly human hair. The dyes according to the present disclosure can also be used in principle for coloring other natural fibers, however, such as, e.g., cotton, jute, sisal, linen, or silk, modified natural fibers such as, for example, regenerated cellulose, nitrocellulose, alkyl or hydroxyalkyl cellulose, or acetyl cellulose.

Preparations (A) and (B) contain all essential components in each case in a cosmetic carrier. The cosmetic carrier can be a suitable aqueous or aqueous-alcoholic carrier. For example, the agent can be applied to the keratinic fibers in the form of a cream, an emulsion, a gel, or also in the form of a surfactant-containing foaming solution, such as, for example, a shampoo, a foam aerosol, a foam formulation, or in the form of some other preparation suitable for use on hair.

The multicomponent packaging unit (kit of parts) according to the present disclosure comprises at least two separately packaged preparations, a first preparation (A) and a second preparation (B).

Preparation (A) in this case comprises, in a cosmetic carrier,
(A1) one or more resorcinol derivatives from the group comprising resorcinol, 2-methylresorcinol, and 4-chlororesorcinol, and
(A2) one or more oxidation dye precursors from the group comprising p-phenylenediamines, p-aminophenols, 2,4,5,6-tetraaminopyrimidines, and 4,5-diaminopyrazoles.

The resorcinol derivatives (A1) are resorcinol, 2-methylresorcinol, and/or 4-chlororesorcinol. A simultaneous straightening and coloring effect could be observed during the use of all three resorcinol derivatives.

Resorcinol is the compound of the formula (I); 2-methylresorcinol is the compound of the formula (II); and 4-chlororesorcinol is the compound of the formula (III).

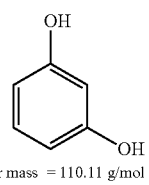

(I)

molar mass = 110.11 g/mol

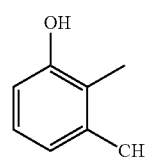

(II)

molar mass = 124.14 g/mol

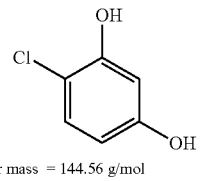

(III)

molar mass = 144.56 g/mol

An optimal reshaping of the keratin fibers and also an intense coloring result are possible thereby, and the resorcinol derivatives (A1) are preferably used in specific amount ranges.

Particularly good results were obtained, if the first preparation (A) comprises one or more resorcinol derivatives (A1) from the group comprising resorcinol, 2-methylresorcinol, and 4-chlororesorcinol in a total amount of about 1.0 from about to about 15.0% by weight, preferably of about 2.0 from about to about 13.0% by weight, more preferably of from about 3.0 to about 12.0% by weight, even more preferably of from about 4.0 to about 11.0% by weight, and very particularly preferably of from about 5.0 to about 10.5% by weight. The calculation basis for these quantitative data in percent by weight in this case is the total weight of all resorcinol derivatives from group (A1), which is placed in relation to the total weight of preparation (A).

In a very particularly preferred embodiment, a multicomponent packaging unit (kit of parts) according to the present disclosure is wherein the first preparation (A) comprises, based on the total weight of preparation (A),
(A1) one or more resorcinol derivatives from the group comprising resorcinol, 2-methylresorcinol, and 4-chlororesorcinol in a total amount of from about 1.0 to about 15.0% by weight, preferably of from about 2.0 to about 13.0% by weight, more preferably of from about 3.0 to about 12.0% by weight, even more preferably of from about 4.0 to about 11.0% by weight, and very particularly preferably of from about 5.0 to about 10.5% by weight.

The oxidation dye precursors (A2) contained furthermore in preparation (A) are compounds from the group comprising p-phenylenediamines, p-aminophenols, 2,4,5,6-tetraaminopyrimidines, and/or 4,5-diaminopyrazoles.

Oxidation dye precursors from the group of p-phenylenediamines are oxidation dye precursors, which can be based on a p-phenylenediamine unit or are derivatives thereof. This means that the p-phenylenediamine unit of the oxidation dye precursors can also be present mono- or polysubstituted, wherein the premise applies that the substitution must be such that an oxidative coupling reaction with the resorcinols (or the additionally contained couplers) to form the dye can still occur.

Particularly suitable oxidation dye precursors from the group of p-phenylenediamines are p-phenylenediamine itself, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, and/or the physiologically acceptable salts of these compounds.

Very especially suitable oxidation dye precursors from the group of p-phenylenediamines are p-toluylenediamine, 2-(2-hydroxyethyl)-p-phenylenediamine, N,N-bis(2-hydroxyethyl)-p-phenylenediamine, 2-methoxymethyl-p-phenylenediamine, and/or the physiological acceptable salts of these compounds.

p-Toluylenediamine is a compound of the formula (IV).

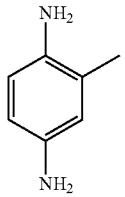

molar mass = 122.17 g/mol

Preferred physiologically acceptable salts of p-toluylenediamine are in particular the hydrochlorides (monohydrochloride×HCl, or dihydrochloride×2HCl), the sulfate (×H$_2$SO$_4$), and the hydrobromides (monohydrobromide×HBr, or dihydrobromide×2HBr) of the compound. p-Toluylenediamine sulfate (formula (IVa)) is very particularly preferred.

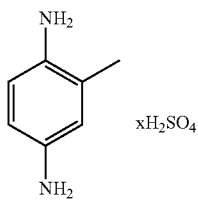

molar mass = 220.25 g/mol 2-(2,5-Diaminophenyl)ethanol is the compound of the formula (V).

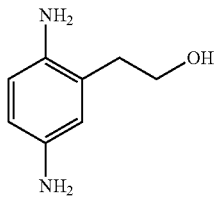

molar mass = 152.20 g/mol

Preferred physiologically acceptable salts of 2-(2,5-diaminophenyl)ethanol are in particular the hydrochlorides (monohydrochloride×HCl, or dihydrochloride×2HCl), the sulfate (×H$_2$SO$_4$), and the hydrobromides (monohydrobromide×HBr, or dihydrobromide×2HBr) of the compound.

2-(2,5-Diaminophenyl)ethanol sulfate (formula (Va)) is very particularly preferred.

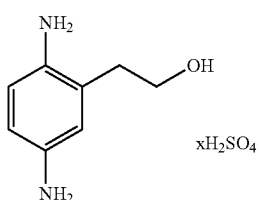

molar mass = 250.27 g/mol

N,N-bis(2-hydroxyethyl)-p-phenylenediamine is a compound of the formula (VI).

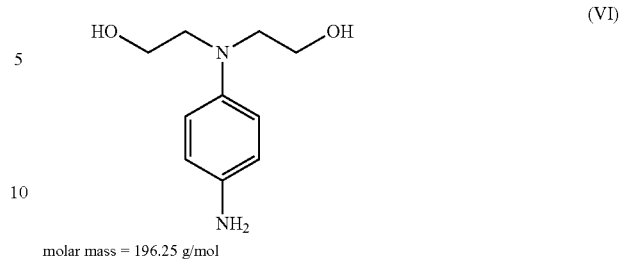

molar mass = 196.25 g/mol

Preferred physiologically acceptable salts of N,N-bis(2-hydroxyethyl)-p-phenylenediamine are in particular the hydrochlorides (monohydrochloride×HCl, or dihydrochloride×2HCl), the sulfate (×H$_2$SO$_4$), and the hydrobromides (monohydrobromide×HBr, or dihydrobromide×2HBr) of the compound. N,N-bis(2-hydroxyethyl)-p-phenylenediamine sulfate (formula (VIa)) is very particularly preferred.

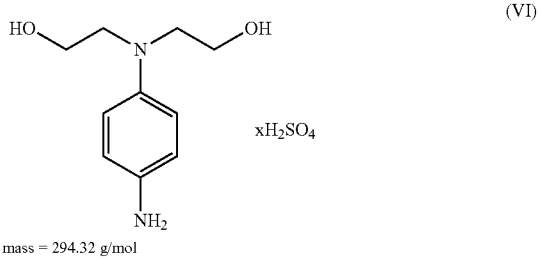

molar mass = 294.32 g/mol

2-Methoxymethyl-p-phenylenediamine is a compound of the formula (VII).

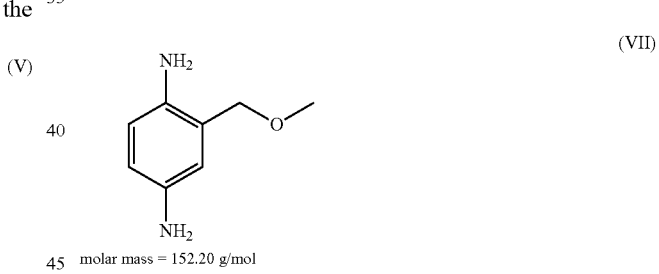

molar mass = 152.20 g/mol

Preferred physiologically acceptable salts of 2-methoxymethyl-p-phenylenediamine are in particular the hydrochlorides (monohydrochloride×HCl, or dihydrochloride×2HCl), the sulfate (×H$_2$SO$_4$), and the hydrobromides (monohydrobromid×HBr, or dihydrobromide×2HBr) of the compound. 2-Methoxymethyl-p-phenylenediamine sulfate (formula (VIIa)) is very particularly preferred.

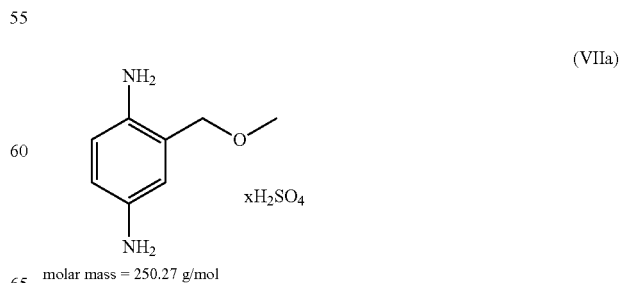

molar mass = 250.27 g/mol

The oxidation dye precursors from the group of p-aminophenols are oxidation dye precursors which can be based on a p-aminophenol unit or are derivatives thereof. This means that the p-aminophenol unit of the oxidation dye precursors can also be present mono- or polysubstituted, wherein the premise applies that the substitution must be such that an oxidative coupling reaction with the resorcinols (or the additionally contained couplers) to form the dye can still occur.

Particularly suitable oxidation dye precursors from the group of p-aminophenols are p-aminophenol itself, 4-amino-3-methylphenol, bis(2-hydroxy-5-aminophenyl)methane, and/or the physiologically acceptable salts of these compounds.

Preferred physiologically acceptable salts of p-aminophenol are in particular the hydrochloride (monohydrochloride×HCl), the sulfate (×½ H$_2$SO$_4$), and the hydrobromide.

Preferred physiologically acceptable salts of 4-amino-3-methylphenol are in particular the hydrochloride (monohydrochloride×HCl), the sulfate (×½ H$_2$SO$_4$), and the hydrobromide.

Preferred physiologically acceptable salts of bis(2-hydroxy-5-aminophenyl)methane are in particular the hydrochloride (monohydrochloride×HCl), the sulfate (×½ H$_2$SO$_4$), and the hydrobromide.

Oxidation dye precursors from the group of 2,4,5,6-tetraaminopyrimidines are oxidation dye precursors which can be based on a 2,4,5,6-tetraaminopyrimidines unit or are derivatives thereof. This means that the 2,4,5,6-tetraaminopyrimidine unit of the oxidation dye precursors can also be present mono- or polysubstituted, wherein the premise applies that the substitution must be such that an oxidative coupling reaction with the resorcinols (or the additionally contained couplers) to form the dye can still occur.

A particularly suitable oxidation dye precursor from the group of 2,4,5,6-tetraaminopyrimidines is 2,4,5,6-tetraaminopyrimidine itself or the physiologically acceptable salts thereof. Oxidation dye precursors from the group of 4,5-diaminopyrazoles are oxidation dye precursors, which can be based on a 4,5-diaminopyrazole unit or are derivatives thereof. This means that the 4,5-diaminopyrazole unit of the oxidation dye precursors can also be present mono- or polysubstituted, wherein the premise applies that the substitution must be such that an oxidative coupling reaction with the resorcinols (or the additionally contained couplers) to form the dye can still occur.

A particularly suitable oxidation dye precursor from the group of the 4,5-diaminopyrazoles is 4,5-diamino-1-(2-hydroxyethyl)pyrazole itself or the physiologically acceptable salts thereof.

4,5-Diamino-1-(2-hydroxyethyl)pyrazole is a compound of the formula (VIII).

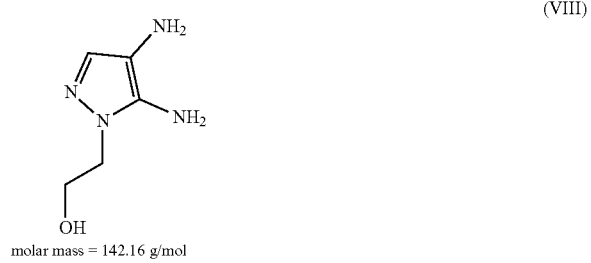

(VIII)

molar mass = 142.16 g/mol

Preferred physiologically acceptable salts of 4,5-diamino-1-(2-hydroxyethyl)-1H-pyrazole are in particular the hydrochlorides (monohydrochloride×HCl, or dihydrochloride×2HCl), the sulfate (×H$_2$SO$_4$), and the hydrobromides (monohydrobromide×HBr, or dihydrobromide×2HBr) of the compound. 4,5-Diamino-1-(2-hydroxyethyl)-1H-pyrazole sulfate (formula (VIIIa)) is very particularly preferred.

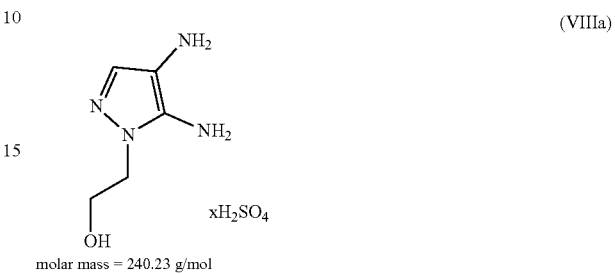

(VIIIa)

molar mass = 240.23 g/mol

The best coloring results could be obtained, if resorcinols (A1) were caused to react with very specific developer-type oxidation dyes (A2). Particularly suitable developer-type oxidation dyes (A2) are selected from the group comprising p-phenylenediamine, p-toluylenediamine, 2-(2-hydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis(2-hydroxy-5-aminophenyl)methane, p-aminophenol, 4-amino-3-methylphenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and/or the physiologically acceptable salts thereof.

Because preparations (A) and (B) come into contact with the hair, and thereby also with the scalp, of the user, the salts of the developer-type oxidation dyes (A2) must be physiologically acceptable. Physiologically acceptable in this context means suitable for use in the cosmetic agent (i.e., for use on human hair and human skin). Particularly preferred physiologically acceptable salts are the hydrochlorides, hydrobromides, hemisulfates, sulfates, p-toluenesulfonates, benzenesulfonates, acetates, lactates, and/or tartrates of the developer-type oxidation dyes (A2). The hydrochlorides (monohydrochloride×HCl or dihydrochlorides×2HCl), sulfates (×½ H$_2$SO$_4$), and hydrobromides (monohydrobromides×HBr or dihydrobromides×2HBr) thereof are very particularly preferred.

In a further very particularly preferred embodiment, a multicomponent packaging unit (kit of parts) according to the present disclosure is wherein first preparation (A) comprises one or more developer-type oxidation dye precursor (A2), which are selected from the group comprising p-phenylenediamine, p-toluylenediamine, 2-(2-hydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis(2-hydroxy-5-aminophenyl)methane, p-aminophenol, 4-amino-3-methylphenol, 4,5-diamino-1-(2-hydroxyethyl)pyrazole, 2,4,5,6-tetraaminopyrimidine, and/or the physiologically acceptable salts thereof.

Preparation (A) preferably comprises the developer-type oxidation dye precursor(s) (A2) in specific amount ranges. Particularly intense colors are obtained, if the first preparation (A) comprises one or more developer-type oxidation dye precursors (A2) in a total amount of from about 0.1 to about 2.5% by weight, preferably of from about 0.2 to about 2.3% by weight, more preferably of from about 0.6 to about 1.7% by weight, and particularly preferably of from about 0.9 to about 1.1% by weight. The calculation basis for these quantitative data in percent by weight in this case is the total weight of all developer-type oxidation dye precursors from group (A2), which is placed in relation to the total weight of preparation (A).

In a further very particularly preferred embodiment, a multicomponent packaging unit (kit of parts) according to the present disclosure is wherein the first preparation (A), based on the total weight of preparation (A), comprises one or more developer-type oxidation dye precursors (A2) in a total amount of from about 0.1 to about 2.5% by weight, preferably of from about 0.2 to about 2.3% by weight, more preferably of from about 0.6 to about 1.7% by weight, and particularly preferably of from about 0.9 to about 1.1% by weight.

A very central feature, of the present disclosure is that in preparation (A) the molar ratio of all resorcinol derivatives (A1) to all developer-type oxidation dye precursors (A2), i.e., the molar ratio (A1)/(A2), is a value of at least about 1.2. In other words, the resorcinol derivatives (A1) in comparison with the developer-type oxidation dye precursors (A2) are used in an at least about 1.2-fold molar excess.

It is assured by the resorcinol derivatives (A1) present in the molar excess that apart from the coloring of the keratin fibers, which occurs by the reaction of resorcinols (A1) with the developer-type oxidation dye precursors (A2) with the formation of dyes, a straightening can also be achieved. Without being restricted to this theory, it is suspected that the straightening is caused by the excess resorcinols (A1), because resorcinols (A1), which are not consumed in the dye formation reaction, can function as swelling agents, as a result of which the shape of the keratin fibers can be influenced permanently.

Without the color shades being adversely affected by the molar excess of resorcinols (A1), in addition a permanent curling or straightening of the keratin fibers is enabled in this way.

The molar mass (unit g/mol) of a compound is defined as mass (unit g) per amount of substance (unit mol).

The amount of substance is understood to mean the quantity of a material portion, based on the number of particles contained therein. The unit for the amount of substance is the base unit of moles (mol or mmol).

The quantitative ratio of resorcinols (A1) to the developer-type oxidation dye precursors (A2) is defined as a molar ratio, because the developer-type oxidation dye precursors (A2) react with a specific number of resorcinol molecules (A1).

Because preparation (B) comprises no oxidation dye precursors (i.e., neither compounds from group (A1) nor compounds from group (A2)), the molar ratio (A1)/(A2) in preparation (A) also corresponds to the molar ratio (A1)/(A2) in the ready-to-use reshaping or coloring agent, which is produced by mixing preparations (A) and (B).

The molar amount of compounds (A1) and (A2), contained in preparation (A), can be obtained in each case by dividing the amounts used by the corresponding molar amounts.

EXAMPLE 100 g of a preparation (A) comprises
(A1) 5.00 g of resorcinol (molar mass=110.11 g/mol) and 3.00 g of 2-methylresorcinol (molar mass=124.14 g/mol).
Therefore, preparation (A) comprises
(A1) 45.4 mmol of resorcinol and 24.2 mmol of 2-methylresorcinol.
Sum=69.6 mmol of resorcinols (A1).

Furthermore, preparation (A) comprises
(A2) 1.50 g of p-toluylenediamine sulfate (molar mass=220.25 g/mol) and 0.50 g of 4,5-diamino-1-(2-hydroxyethyl)-1H-pyrazole sulfate (molar mass=240.23 g/mol)
Therefore, preparation (A) comprises
(A2) 6.81 mmol of p-toluylenediamine sulfate and 2.08 mmol of 4,5-diamino-1-(2-hydroxyethyl)-1H-pyrazole sulfate.
Sum=8.89 mmol of oxidation dye precursors of group (A2).
The molar ratio (A1)/(A2) in preparation (A) is 69.6 mmol/8.89 mmol=7.83.
The molar ratio (A1)/(A2) in the ready-to-use agent (which is a mixture of preparations (A) and (B)) is also 7.83.

So that resorcinol derivatives (A1) can cause both a reshaping and coloring of the keratin fibers, they must be contained in preparation (A) in comparison with the developer-type oxidation dyes (A2) in an at least 1.2-fold molar excess.

Even starting at an about 1.2-fold molar excess, a reshaping effect is observed in addition to the coloring effect. The reshaping effect however is even more pronounced, if the molar excess of resorcinols, i.e., the ratio (A1)/(A2), in preparation (A) is increased still further. Surprisingly, the coloring result is not adversely affected by the increase in the amount of the resorcinols from group (A1) contained in preparation (A).

A very particularly good coloring and reshaping could be observed, if the molar ratio of all resorcinol derivatives (A1), contained in the agent, to all developer-type oxidation dyes (A2), contained in the agent, i.e., the molar ratio (A1)/(A2), had a value of from about 1.3 to about 60.0, preferably of from about 1.5 to about 50.0, preferably of from about 2.0 to about 45.0, more preferably of from about 4.0 to about 35.0, and particularly preferably of from about 7.0 to about 32.0.

In a further explicitly very particularly preferred embodiment, a multicomponent packaging unit (kit of parts) according to the present disclosure is therefore wherein the molar ratio of all resorcinol derivatives (A1), contained in preparation (A), to all developer-type oxidation dye precursors (A2), contained in preparation (A), i.e., the molar ratio (A1)/(A2), has a value of from about 1.3 to about 60.0, preferably of from about 1.5 to about 50.0, more preferably of from about 2.0 to about 45.0, even more preferably of from about 4.0 to about 35.0, and particularly preferably of from about 7.0 to about 32.0.

Apart from the oxidation dye precursors from the aforementioned groups (A1) and (A2), preparation (A) can contain in addition also still one or more couplers, which are structurally different from resorcinol derivatives (A1). Additional couplers can be used to modify the desired hue.

Coupler components alone during oxidative dyeing cause no significant coloring but always require the presence of developer components. Coupler components permit at least one substitution of a chemical group of the coupler by the oxidized form of the developer component. In this regard, covalent bonds form between the coupler and developer component.

Preferably at least one compound from one of the following classes is selected as a coupler component suitable as contemplated herein:
m-aminophenol and/or derivatives thereof,
m-diaminobenzene and/or derivatives thereof,
o-diaminobenzene and/or derivatives thereof,
o-aminophenol derivatives such as, for example, o-aminophenol, naphthalene derivatives with at least one hydroxy group,
di- or trihydroxybenzene and/or derivatives thereof,
pyridine derivatives,
pyrimidine derivatives,
monohydroxyindole derivatives and/or monoaminoindole derivatives,
monohydroxyindoline derivatives and/or monoaminoindoline derivatives,
pyrazolone derivatives such as, for example, 1-phenyl-3-methylpyrazol-5-one,
morpholine derivatives such as, for example, 6-hydroxybenzomorpholine or 6-amino benzo-morpholine,
quinoxaline derivatives, such as, for example, 6-methyl-1,2,3,4-tetrahydroquinoxaline.

Mixtures of two or more compounds from one or more of these classes are also included as contemplated herein in the context of this embodiment.

The additional couplers form very intense colors in combination with the oxidation dye precursors from group (A2). Preferred are couplers to be used in addition, which are selected from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)-amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, and/or 7-hydroxyindoline, and the physiologically acceptable salts thereof.

In a further embodiment, a multicomponent packaging unit (kit of parts) according to the present disclosure is wherein preparation (A) comprises in addition at least one or more couplers from the group, formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-2-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, and/or the physiologically acceptable salts thereof.

Preparation (A) in principle can contain in addition one or more coupler components from the aforementioned group in a total amount of from about 0.001 to about 3.0% by weight, preferably of from about 0.025 to about 1.5% by weight, more preferably of from about 0.05 to about 1.0% by weight, and particularly preferably of from about 0.1 to about 0.5% by weight, based on the total weight of preparation (A).

For a further shade development, preparation (a) can also contain in addition at least one direct dye from the group of anionic, nonionic, and/or cationic dyes.

Particularly preferably, these concern one or more nonionic direct dyes from the group comprising HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Suitable cationic direct dyes are cationic triphenylmethane dyes, such as, for example, Basic Blue 7, Basic Blue 26, Basic Violet 2, and Basic Violet 14, aromatic systems, substituted with a quaternary nitrogen group, such as, for example, Basic Yellow 57, Basic Red 76, Basic Blue 99, Basic Brown 16, and Basic Brown 17, cationic anthraquinone dyes, such as HC Blue 16 (Bluequat B), and direct dyes, comprising a heterocycle that has at least one quaternary nitrogen atom, particularly Basic Yellow 87, Basic Orange 31, and Basic Red 51. The cationic direct dyes, marketed under the trademark Arianor, are also suitable cationic direct dyes as contemplated herein.

For example, one or more compounds can be selected as suitable anionic dyes or acid dyes from the following group: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D&C Brown No. 1), Acid Red 14 (C.I. 14720), Acid Red 18 (E124, Red 18; CI 16255), Acid Red 27 (E 123, CI 16185, C-Rot 46, Echtrot D, FD&C Red No. 2, Food Red 9, Naphtholrot S), Acid Red 33 (Red 33, Fuchsia Red, D&C Red 33, CI 17200), Acid Red 35 (CI C.I. 18065), Acid Red 51 (CI 45430, Pyrosin B, tetraiodofluorescein, Eosin J, Iodeosin), Acid Red 52 (CI 45100, Food Red 106, Solar Rhodamine B, Acid Rhodamine B, Red n° 106, Pontacyl Brilliant Pink), Acid Red 73 (CI 27290), Acid Red 87 (Eosin, CI 45380), Acid Red 95 (CI 45425, Erythrosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blau V, CI 42051), Acid Blue 7 (CI 42080), Acid Blue 104 (CI 42735), Acid Blue 9 (E 133, Patentblau AE, Amidoblau AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Food Green 1), Acid Green 5 (CI 42095), Acid Green 9 (C.I. 42100), Acid Green 22 (C. 1.42170), Acid Green 25 (CI 61570, Japan Green 201, D&C Green No. 5), Acid Green 50 (Brillantsauregrün BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

Apart from preparation (A), the multicomponent packaging unit (kit of parts) according to the present disclosure comprises, furthermore, preparation (B) packaged separately from preparation (A). Preparation (B) comprises hydrogen peroxide in a cosmetic carrier (B1). The dyes form in an oxidative coloring process by the reaction of hydrogen peroxide with the oxidation dye precursors. To prevent a premature reaction, compounds (A1) and (A2) cannot be stored together with hydrogen peroxide.

In a further preferred embodiment, hydrogen peroxide itself is used as an aqueous solution in preparation (B). The concentration of a hydrogen peroxide solution in preparation (B) is determined, on the one hand, by legal requirements and, on the other, by the desired effect; preferably, from about 6 to about 12% by weight solutions in water are used. Preparations (B) preferred as contemplated herein are wherein they contain from about 0.1 to about 6.0% by weight, preferably from about 0.15 to about 5.0% by weight, more preferably from about 0.2 to about 4.5% by weight, and very particularly preferably from about 0.3 to about 4.2% by weight of hydrogen peroxide, based in each case on the total weight of preparation (B).

In a further explicitly very particularly preferred embodiment, a multicomponent packaging unit (kit of parts) according to the present disclosure is therefore wherein second preparation (B), based on the total weight of preparation (B), comprises hydrogen peroxide in an amount of from about 0.1 to about 12.0% by weight, preferably of from about 0.15 to about 5.0% by weight, more preferably of from about 0.2 to about 4.5% by weight, and very particularly preferably of from about 0.3 to about 4.2% by weight.

Keratinic fibers can be both colored oxidatively and permanently reshaped by applying the ready-to-use reshaping and coloring agent, i.e., by using the mixture of preparations (A) and (B). The use of further reducing agents, as they are obligatory for waving compositions or straightening products known from the prior art, can be omitted for this reason. This nonuse of reducing agents makes reshaping and coloring possible with the greatest possible protection of the keratin fibers. It was therefore possible to prevent hair damage optimally with the use of the multicomponent packaging unit according to the present disclosure.

For this reason, multicomponent packaging units (kit of parts) are very particularly preferred that are wherein preparation (A) is free of reducing agents. Preparation (B) comprises hydrogen peroxide as the oxidizing agent, so that the addition of reducing agents to preparation (B) would cause undesirable reactions between oxidizing agents and reducing agents and accordingly is likewise not appropriate. A preparation (A) that is free of reducing agents is understood to be a preparation whose total content of reducing agents from the group comprising thioglycolic acid, thiolactic acid, cysteine, and the salts of said compounds, based on the total weight of preparation (A), is below about 1.0% by weight, preferably below about 0.5% by weight, more preferably below about 0.1% by weight, and particularly preferably below about 0.05% by weight.

In a further very particularly preferred embodiment, a multicomponent packaging unit (kit of parts) according to the present disclosure is wherein first preparation (A), based on the total weight of preparation (A), comprises reducing substances from the group comprising thioglycolic acid, thiolactic acid, cysteine, and the salts of said compounds in a total amount of less than about 1.0% by weight, preferably of less than about 0.5% by weight, more preferably of less than about 0.1% by weight, and particularly preferably of less than about 0.05% by weight.

To prevent the autoxidation of oxidation dye precursors (A2), preparation (A) can contain small amounts of reducing agent from the group of sulfites (e.g., sodium sulfite, sodium bisulfite, ammonium sulfite, potassium sulfite, etc.) or ascorbic acid. The amounts used of these reducing agents in this case are below about 1.0% by weight, preferably below about 0.5% by weight, even more preferably below about 0.1% by weight (calculated in each case as the total weight of the reducing agents from the group of sulfites and ascorbic acid based on the total weight of preparation (A)). These reducing agents do not have a reshaping effect on the keratinic fibers, however, in particular in these low amounts used, but should only prevent an unattractive discoloration of preparation (A) caused by the reaction of oxidation dye precursors (A2) with atmospheric oxygen. To minimize hair damage completely, it is then of advantage to avoid these reducing agents as well.

In a further very particularly preferred embodiment, a multicomponent packaging unit (kit of parts) according to the present disclosure is wherein first preparation (A), based on the total weight of preparation (A), comprises reducing substances from the group comprising thioglycolic acid, thiolactic acid, cysteine, and the salts of said compounds, sodium sulfite, sodium bisulfite, ammonium sulfite, ammonium bisulfite, potassium sulfite, and potassium bisulfite, in a total amount of less than about 1.0% by weight, preferably of less than about 0.5% by weight, more preferably of less than about 0.1% by weight, and particularly preferably of less than about 0.05% by weight.

To improve the reshaping and coloring result further, it emerged as advantageous if preparation (A) and/or preparation (B) contain at least one further swelling agent. Used preferably as swelling agents is a compound from the group comprising urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example, propylene glycol monoethyl ether, carbonates, hydrogen carbonates, diols and triols, and in particular 1,2-diols and 1,3-diols such as, for example, 1,2-propanediol, 1,2-pentanediol, 1,2-hexanediol, 1,2-dodecanediol, 1,3-propanediol, 1,6-hexanediol, 1,5-pentanediol, 1,4-butanediol, but sorbitol or pyrrolidone carboxylic acid as well. An especially advantageous hair straightening and especially advantageous coloring results are achieved by using a swelling agent from the group comprising urea, glycerol (propane-1,2,3-triol), sorbitol (D-glucitol), and/or pyrrolidone carboxylic acid (5-oxopyrrolidine-2-carboxylic acid), in particular urea. The use of these specific swelling agents is therefore preferred as contemplated herein.

The weight proportion of the swelling agent in terms of the total weight of preparation (A) or preparation (B) is preferably from about 0.2 to about 15% by weight, preferably from about 1.0 to about 12% by weight, and in particular from about 2.0 to about 10% by weight.

In a further particularly preferred embodiment, a multi-component packaging unit (kit of parts) according to the present disclosure is therefore wherein preparation (A) and/or preparation (B) contain at least one swelling agent, preferably from the group comprising urea, glycerol (propane-1,2,3-triol), sorbitol (D-glucitol), and/or pyrrolidone carboxylic acid (5-oxopyrrolidine-2-carboxylic acid).

In order to intensify the lightening effect, preparations (A) and/or (B) can contain further bleach boosters such as, for example, tetraacetylethylenediamine (TAED), 1,5-diacetyl-2,4-dioxohexahydro-1,3,5-triazine (DADHT), tetraacetyl glycoluril (TAGU), N-nonanoylsuccinimide (NOSI), n-nonanoyl- or isononanoyloxybenzenesulfonate (n- or i-NOBS), phthalic anhydride, triacetin, ethylene glycol diacetate, and 2,5-diacetoxy-2,5-dihydrofuran, and carbonate salts or hydrogen carbonate salts, in particular ammonium hydrogen carbonate, ammonium carbonate, sodium hydrogen carbonate, disodium carbonate, potassium hydrogen carbonate, dipotassium carbonate, and calcium carbonate, and nitrogen-containing, heterocyclic bleach boosters, such as 4-acetyl-1-methylpyridinium-p-toluenesulfonate, 2-acetyl-1-methylpyridinium-p-toluenesulfonate, and N-methyl-3,4-dihydroisoquinolinium-p-toluenesulfonate.

To increase the lightening further, at least one SiO2 compound, such as silicic acid or silicates, in particular water glasses, can also be added in addition to preparations (A) and/or (B). In this case, coloring preparation (A) and/or oxidizing agent preparation (B) can contain the SiO2 compound. It can be preferred as contemplated herein to use the SiO2 compounds in amounts of from about 0.05% by weight to about 15% by weight, particularly preferably in amounts of from about 0.15% by weight to about 10% by weight, and very particularly preferably in amounts of from about 0.2% by weight to about 5% by weight, based in each case on the total weight of coloring preparation (A) or on the total weight of oxidizing agent preparation (B). The quantitative data in this case indicate the content of the SiO2 compounds (without their water component) in the agents.

Preparations (A) and/or (B), furthermore, can contain additional active substances, auxiliary substances, and additives in order to improve the coloring or lightening performance and to set other desired properties of the agents.

The ready-to-use coloring agents are preferably provided as a liquid preparation and another surface-active substance is therefore optionally added in addition to the agents, wherein such surface-active substances are called surfactants or emulsifiers depending on the field of application: They are preferably selected from anionic, zwitterionic, amphoteric, and nonionic surfactants and emulsifiers.

Agents suitable as contemplated herein are wherein the agent comprises in addition at least one anionic surfactant. Preferred anionic surfactants are fatty acids, alkyl sulfates, alkyl ether sulfates, and ether carboxylic acids having 10 to 20 C atoms in the alkyl group and up to 16 glycol ether groups in the molecule.

Agents suitable as contemplated herein are wherein the agent comprises in addition at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. A preferred zwitterionic surfactant is known by the INCI name Cocamidopropyl Betaine.

Agents suitable as contemplated herein are wherein the agent comprises in addition at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkyl aminopropionate, cocoacylaminoethyl aminopropionate, and C12-C18 acylsarcosine.

It has proven advantageous, furthermore, for the agents to contain other non-ionogenic surface-active substances. Preferred nonionic surfactants are alkyl polyglycosides and alkylene oxide adducts to fatty alcohols and fatty acids with in each case 2 to 30 mol of ethylene oxide per mole of fatty alcohol or fatty acid. Preparations with excellent properties are likewise obtained if they contain fatty acid esters of ethoxylated glycerol as the nonionic surfactants.

The nonionic, zwitterionic, or amphoteric surfactants are used in proportions of from about 0.1 to about 45% by weight, preferably from about 1 to about 30% by weight, and very particularly preferably of from about 1 to about 15% by weight, based on the total amount of the ready-to-use agents.

The ready-to-use color changing agents can also contain at least one thickener. There are no basic restrictions in regard to these thickeners. Both organic and purely inorganic thickeners may be used.

Suitable thickeners are anionic, synthetic polymers, cationic, synthetic polymers, naturally occurring thickeners, such as nonionic guar gums, scleroglucan gums or xanthan gums, gum arabic, gum ghatti, karaya gum, tragacanth gum, carrageenan gum, agar-agar, locust bean gum, pectins, alginates, starch fractions, and derivatives such as amylose, amylopectin, and dextrins, as well as cellulose derivatives such as, for example, methylcellulose, carboxyalkylcelluloses, and hydroxyalkylcelluloses, nonionic, fully synthetic polymers, such as polyvinyl alcohol or polyvinylpyrrolidinone; as well as inorganic thickeners, in particular phyllosilicates such as, for example, bentonite, in particular smectites, such as montmorillonite or hectorite.

It has proven to be advantageous, furthermore, if the dyeing agents, particularly if they contain hydrogen peroxide in addition, contain at least one stabilizer or complexing agent. Particularly preferred stabilizers are phenacetin, alkali benzoates (sodium benzoate), and salicylic acid. Furthermore, all complexing agents in the prior art can be used. Complexing agents preferred as contemplated herein are nitrogen-containing polycarboxylic acids, particularly EDTA and EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

Further, the agents according to the present disclosure can contain other active substances, auxiliary substances, and additives such as, for example, nonionic polymers such as, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched or cyclic, crosslinked or noncrosslinked polyalkylsiloxanes (such as dimethicones or cyclomethicones), polyarylsiloxanes, and/or polyalkylarylsiloxanes, particularly polysiloxanes with organofunctional groups, such as substituted or unsubstituted amines (amodimethicones), carboxyl, alkoxy, and/or hydroxyl groups (dimethicone copolyols), linear polysiloxane(A)-polyoxyalkylene (B) block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidinone copolymers quaternized with diethyl sulfate, vinylpyrrolidinone-imidazolinium-methochloride copolymers, and quaternized polyvinyl alcohol; zwitterionic and amphoteric polymers; anionic polymers such as, for example, polyacrylic acids or crosslinked polyacrylic acids; structurants such as glucose, maleic acid, and lactic acid, hair-conditioning compounds such as phospholipids, for example, lecithin and kephalins; perfume oils, dimethyl isosorbide, and cyclodextrins; fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; vegetable oils; light stabilizers and UV blockers; active substances such as panthenol, pantothenic acid, pantolactone, allantoin, pyrrolidinone carboxylic acids and salts thereof, as well as bisabolol; polyphenols, particularly hydroxycinnamic acids, 6,7-dihydroxycoumarins, hydroxybenzoic acids, catechins, tannins, leukoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ethers, carbonates, hydrogen carbonates, guanidines, ureas, and primary, secondary, and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, $N_2O$, dimethyl ether, $CO_2$, and air.

The selection of these additional substances is made by the skilled artisan according to the desired properties of the agents. In regard to other facultative components and the employed amounts of said components, reference is made expressly to relevant handbooks known to the skilled artisan. The additional active and auxiliary substances are used in the agents according to the present disclosure preferably in each case in amounts of from about 0.0001 to about 25% by weight, in particular of from about 0.0005 to about 15% by weight, based in each case on the total weight of coloring preparation (A) and/or oxidizing agent preparation (B).

The coloring and reshaping of the keratinic fibers can occur at pH values in the range of 2 to 12, but a coloring and reshaping in the alkaline range is preferred. In this case the pH value of the ready-to-use agent, i.e., the mixture of preparations (A) and (B), is essential for the coloring and reshaping result. For reasons of stability, preparation (B), which comprises the oxidizing agent hydrogen peroxide, is adjusted to an acidic pH value of from about 1.0 to about 6.0, preferably of from about 2.0 to about 5.0. Preparation (A) is preferably adjusted to an alkaline pH value of from about 7.0 to about 11.5, preferably of from about 8.0 to about 10.5. The pH value of the mixture of preparations (A) and (B) is also preferably in the alkaline range of from about 7.5 to about 10.5.

All compounds capable of donating a proton (monobasic acid) or a number of protons (polybasic acid) are suitable in principle for adjusting the acidic pH value. For example, mineral acids such as hydrochloric acid, sulfuric acid, and phosphoric acid, preferably in their water-diluted form, can be used as inorganic acids. Organic acids can also be used in the formulations according to the present disclosure. Typical representatives of organic acids are aliphatic mono- and dicarboxylic acids such as, for example, acetic acid, propionic acid, oxalic acid, and 1,3-propanedioic acid and aromatic carboxylic acids such as, for example, benzoic acid. Other organic acids according to the present disclosure are hydroxycarboxylic acids such as glycolic acid, citric acid, tartaric acid, malic acid, and lactic acid. Unsaturated mono- or dicarboxylic acids such as, for example, fumaric acid, or α-ketocarboxylic acids such as, for example, pyruvic acid (2-oxopropionic acid) are included as contemplated herein.

Because of legal requirements for cosmetic agents and requirements in terms of formulation techniques, however, low-odor acids, permitted for use in cosmetics, are most suitable for the development of hair treatment agents with a good coloring performance. Hair coloring agents that contain at least one acid selected from citric acid, tartaric acid, malic acid, lactic acid, 1-hydroxyethane-1,1-diphosphonic acid, 2,6-dipicolinic acid, and benzoic acid, are therefore preferred.

The alkalinizing agents that can be used as contemplated herein to adjust the preferred pH values, in particular the pH value of preparation (A), can be selected from among ammonia, alkanolamines, basic amino acids, and inorganic alkalinizing agents such as alkali (alkaline earth) metal hydroxides, alkali (alkaline earth) metal metasilicates, alkali (alkaline earth) metal phosphates, and alkali (alkaline earth) metal hydrogen phosphates. Preferred inorganic alkalinizing agents are magnesium carbonate, sodium hydroxide, potassium hydroxide, sodium silicate, and sodium metasilicate. Organic alkalinizing agents that can be used as contemplated herein are preferably selected from monoethanolamine, 2-amino-2-methylpropanol, and triethanolamine. The basic amino acids that can be used as alkalinizing agents according to the present disclosure are preferably selected from the group formed by arginine, lysine, ornithine, and histidine, especially preferably arginine. It has emerged in the context of studies for the present disclosure, however, that, furthermore, agents preferred as contemplated herein are wherein they contain in addition an organic alkalinizing agent. An embodiment of the first subject of the present disclosure is wherein the agent comprises in addition at least one alkalinizing agent, which is selected from the group formed by ammonia, alkanolamines, and basic amino acids, particularly by ammonia, monoethanolamine, and arginine, or the acceptable salts thereof.

The pH values measured in the context of the present disclosure are pH values measured at a temperature of 22° C. Glass electrodes in particular, which can made, for example, in the shape of a single-rod measuring chain, are suitable for measuring the pH value.

The preparations, according to an exemplary embodiment, of the multicomponent packaging unit (kit of parts) are preparations (A) and (B), because their mixing and application are responsible for the coloring and reshaping result of the keratin fibers. To achieve further effects, the multicomponent packaging unit can also comprise still further preparations, however, such as, for example, a third conditioner preparation (C), which can contain care-providing ingredients such as cationic polymers or cationic surfactants.

To simplify the application process and to shorten the application time, it is preferable, however, if the multicomponent packaging unit according to the present disclosure comprises precisely these two preparations (A) and (B) and comprises no third preparation, which would be applied to the keratinic fibers as a pre- or aftertreatment agent.

In a further particularly preferred embodiment, a multicomponent packaging unit (kit of parts) according to the present disclosure is wherein it comprises two separately packaged preparations (A) and (B).

This means that the multicomponent packaging unit comprises precisely the two separately packaged preparations (A) and (B) and no other preparation (C). The multicomponent packaging units according to the present disclosure can be used in methods for the simultaneous reshaping and coloring of keratinic fibers, in particular human hair.

A second subject of the present disclosure is a method for the reshaping and coloring of human hair, comprising the following steps:
(I) Preparing a ready-to-use reshaping and coloring agent by mixing a preparation (A) with a preparation (B), preparations (A) and (B) being disclosed in detail in the description of the first subject according to the present disclosure;
(II) Applying the ready-to-use reshaping and coloring agent, prepared in step (I), to the hair;
(III) Mechanically reshaping the hair;
(IV) Rinsing the hair;
(V) Optionally drying the hair.

To prepare the ready-to-use reshaping and coloring agent, preparations (A) and (B) can be mixed in a weight ratio of from about 1:10 to about 10:1. It is especially advantageous in regard to an optimal reshaping and coloring, if preparations (A) and (B) are mixed in a quantitative ratio (A)/(B) of from about 3:1 to about 1:3, preferably of from about 2:1 to about 1:2, and particularly preferably of from about 1.5:1 to about 1:1.5.

In a particularly preferred embodiment, a method includes in step (I) preparations (A) and (B) are mixed in a quantitative ratio (A)/(B) of from about 3:1 to about 1:3, preferably of from about 2:1 to about 1:2, and particularly preferably of from about 1.5:1 to about 1:1.5.

During the contact time of the ready-to-use agent (i.e., the mixture of preparations (A) and (B)) on the fiber or in the case of the mechanical reshaping, it can be advantageous to support the reshaping and coloring process by supplying heat. Heat may be supplied by an external heat source such as, e.g., warm air from a warm air blower, and also, in particular in the case of use on living subjects, by the body temperature of the subject. In the case of the latter option, the treated portion is usually covered with a hood. A contact phase or mechanical reshaping at room temperature is also included as contemplated herein. The temperature during the contact time or during the reshaping is in particular between from about 20° C. and about 80° C., in particular between from about 30° C. and about 65° C. Increasing the temperature above about 65° C., in particular above about 80° C., is not of advantage to prevent hair damage.

In another particularly preferred embodiment, a method according to the present disclosure is therefore wherein in step (III) the mechanical reshaping of the hair occurs at a temperature of from about 20 to about 80° C., preferably at a temperature of from about 30 to about 65° C.

The mechanical reshaping carried out in step (III) of the method according to the present disclosure can be a waving or curling of the hair; this is achieved, for example, in that the hair has been wound on curlers or rollers before use of the agent and the agent now acts on the hair on the curlers. It is preferred, however, if the mechanical reshaping is a straightening of the hair, which can occur, for example, by combing or pulling the hair straight with a comb or brush.

In a further particularly preferred embodiment, a method according to the present disclosure is therefore wherein in step (III) the mechanical reshaping is a straightening of the hair, which occurs by combing or pulling the hair straight with a comb or brush.

The ready-to-use reshaping and coloring agent can be used on the hair for a time period of from about 5 to about 60 minutes, preferably for about 10 to about 55 minutes, and particularly preferably for about 25 to about 50 minutes.

After the contact time ends or after completion of the mechanical reshaping, the reshaping and coloring agent in step (IV) is rinsed out of the hair with water or a cleansing product. A commercial shampoo, in particular, may serve here as a cleansing agent, wherein the cleansing agent can be omitted and the rinsing-out operation can occur with water, particularly if the reshaping and coloring agent possesses a highly surfactant-containing carrier.

Optionally, the hair can then be dried in step (V), either at room temperature or with the use of a heating hood or a hair dryer.

The method according to the present disclosure is characterized by the steps (I) to (IV) and by the optional step (V). The precise sequence of the steps can be varied according to the user's wishes.

In a particularly preferred embodiment, a method according to the present disclosure is wherein the sequence of the steps in the method is the following: step (I), followed by step (II), followed by step (III), followed by step (IV), followed by step (V).

In the context of this embodiment, a method according to the present disclosure is therefore characterized by the order of the steps in the indicated sequence:
(I) Preparing a ready-to-use reshaping and coloring agent by mixing a preparation (A) with a preparation (B), preparations (A) and (B) being disclosed in detail in the description of the first subject according to the present disclosure;
(II) Applying the ready-to-use reshaping and coloring agent, prepared in step (I), to the hair;
(III) Mechanically reshaping the hair, which is still being acted upon by the ready-to-use reshaping and coloring agent;
(IV) Rinsing the hair;
(V) Optionally drying the hair.

In a likewise particularly preferred embodiment, a method according to the present disclosure is wherein the sequence of the steps in the method is the following: step (I), followed by step (II), followed by step (IV), followed by step (III), followed by step (V).

In the context of this second, likewise particularly preferred embodiment, a method according to the present disclosure is therefore characterized by the order of the steps in the indicated sequence:

(I) Preparing a ready-to-use reshaping and coloring agent by mixing a preparation (A) with a preparation (B), preparations (A) and (B) being disclosed in detail in the description of the first subject according to the present disclosure;
(II) Applying the ready-to-use reshaping and coloring agent, prepared in step (I), to the hair;
(III) Rinsing the hair;
(IV) Mechanically reshaping the hair;
(V) Optionally drying the hair.

This second embodiment is more convenient for the user, because the mechanical straightening (for example, by combing or pulling straight with a comb or brush) can also occur after the ready-to-use coloring and reshaping agent was again rinsed out of the hair.

It could be determined in the context of this embodiment that the resorcinol derivatives (A1), diffusing into the hair and present in excess within the fibers, also cause a straightening of the hair, if the reshaping and coloring agent itself was again already rinsed off the hair.

Preparations (A) and (B), previously disclosed in detail in the description of the first subject according to the present disclosure, are excellently suitable for the simultaneous straightening and coloring of keratinic fibers.

A further subject of the present disclosure therefore is the use of an agent, prepared by mixing two separately packaged preparations (A) and (B), for reshaping and coloring human hair, wherein preparations (A) and (B) were disclosed in detail in the description of the first subject according to the present disclosure.

A further subject is lastly the use of resorcinol, 2-methylresorcinol, and/or 4-chlororesorcinol in an oxidative hair coloring agent for the reshaping of hair.

The statements made about the multicomponent packaging units (kits of parts) according to the present disclosure apply mutatis mutandis in regard to other preferred embodiments of the method according to the present disclosure and the use thereof.

EXAMPLES

1. Formulations

The following formulations were prepared; all data, unless specified otherwise, are given in percent by weight of active substance.

Preparation (A)

|  | V | E |
|---|---|---|
| Cetearyl alcohol (C16-C18 fatty alcohols) | 8.5 | 8.5 |
| C12-C18 fatty alcohols | 2.0 | 2.0 |
| Texapon NSO (lauryl ether sulfate, sodium sulfate, 27.5% solution in water, INCI: Sodium Laureth Sulfate) | 20.0 | 20.0 |
| Cocoamidopropyl betaine (30% solution in water) | 12.5 | 12.5 |
| Ceteareth-20 | 0.75 | 0.75 |
| Ammonium sulfite | 1.0 | 1.0 |
| Resorcinol (A1) |  | 10.00 (90 mmol) |
| p-Toluylenediamine sulfate (A2) |  | 1.10 (3 mmol) |
| Molar ratio (A1)/(A2) |  | 30 |
| Ammonia | to pH 8.5 | to pH 8.5 |
| Water | to 100 | to 100 |

Preparations (B)

|  | OX |
|---|---|
| Hydrogen peroxide | 3.0 |
| Water | to 100 |

Preparation (A) in each case was mixed with preparations (B) in the quantitative ratio of 1:1.

The strands, used in these tests, were curled hair strands of the same length. Each of these ready-to-use agents was applied in each case to a curled hair strand (Kerling 6-0) (4 g of coloring agent per 1 g of hair), left there for 45 minutes, and in the process pulled straight with a comb several times. The strands were then rinsed with warm water, again combed straight with a comb, and dried with a hair dryer.

After the drying, each strand was assessed on the background of a scaled template; the length of the hair strand was determined using the scale.

The strands were then washed with a shampoo and dried hanging in a climatic chamber. After drying, the strands were again assessed on the background of a scaled template, and the length of the hair strands was again determined using the scale.

The longer the hair strands, the less it is curled and the straighter the strand.

| Preparation (A) + preparation (B) | V + OX | E + OX |
|---|---|---|
| Length before washing | 15.0 cm | 15.0 cm |
| Length after washing | 13.5 cm | 15.0 cm |
| Evaluation of straightening | + | +++ |

+ = poor
++ = average
+++ = good

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A multicomponent packaging unit for reshaping and coloring keratinic fibers, the multicomponent packaging unit comprising at least two separately packaged preparations (A) and (B), wherein the first preparation (A) contains, in a cosmetic carrier, (A1) one or more resorcinol derivatives from the group comprising resorcinol, 2-methylresorcinol, and 4-chlororesorcinol, and (A2) one or more oxidation dye precursors from the group comprising p-phenylenediamines, p-aminophenols, 2,4,5,6-tetraaminopyrimidines, 4,5-diaminopyrazoles, and/or the physiologically acceptable salts thereof, and the second preparation (B) contains, in a cosmetic carrier, (B1) hydrogen peroxide, wherein the molar ratio of all resorcinol derivatives (A1), contained in the first preparation (A), to all developer-type oxidation dyes (A2), contained in the first preparation (A) define the molar ratio (A1)/(A2) having a value of at least about 1.2; and wherein the combination of the first preparation (A) and the second preparation (B) is adapted to simultaneously color the keratinic fibers and chemically reshape the keratinic fibers.

2. The multicomponent packaging unit according to claim 1, wherein the first preparation (A) contains, based on the total weight of preparation (A), (A1) one or more resorcinol derivatives from the group comprising resorcinol, 2-methylresorcinol, and 4-chlororesorcinol in a total amount of from about 1.0 to about 15.0% by weight.

3. The multicomponent packaging unit according to claim 1, wherein the first preparation (A) contains (A2) one or more developer-type oxidation dye precursors, which are selected from the group comprising p-phenylenediamine, p-toluylenediamine, 2-(2-hydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis(2-hydroxy-5-aminophenyl)methane, p-aminophenol, 4-amino-3-methylphenol, 4,5-diamino-1-(2-hydroxyethyl) pyrazole, 2,4,5,6-tetraaminopyrimidine, and/or the physiologically acceptable salts thereof.

4. The multicomponent packaging unit according to claim 1, wherein the first preparation (A), based on the total weight of preparation (A), contains (A2) one or more developer-type oxidation dye precursors in a total amount of from about 0.1 to about 2.5% by weight.

5. The multicomponent packaging unit according to claim 1, wherein the molar ratio of all resorcinol derivatives (A1), contained in preparation (A), to all developer-type oxidation dye precursors (A2), contained in preparation (A) define the molar ratio (A1)/(A2) having a value of from about 1.3 to about 60.0.

6. The multicomponent packaging unit according to claim 1, wherein the second preparation (B), based on the total weight of preparation (B), contains hydrogen peroxide in an amount of from about 0.1 to about 12.0% by weight.

7. The multicomponent packaging unit according to claim 1, wherein first preparation (A), based on the total weight of preparation (A), contains reducing substances from the group comprising thioglycolic acid, thiolactic acid, cysteine, and the salts of said compounds in a total amount of less than from about 1.0% by weight.

8. The multicomponent packaging unit according to claim 1, wherein preparation (A) and/or preparation (B) contain at least one swelling agent.

9. The multicomponent packaging unit according to claim 1, wherein the multicomponent packaging unit comprises two separately packaged preparations (A) and (B).

10. A method for reshaping and coloring human hair, the method comprising the steps of:

(I) preparing a ready-to-use reshaping and coloring agent by mixing a preparation (A) with a preparation (B), preparations (A) and (B) being defined as follows:

the preparation (A) contains, in a cosmetic carrier, (A1) one or more resorcinol derivatives from the group comprising resorcinol, 2-methylresorcinol, and 4-chlororesorcinol, and (A2) one or more oxidation dye precursors from the group comprising p-phenylenediamines, p-aminophenols, 2,4,5,6-tetraaminopyrimidines, 4,5-diaminopyrazoles, and/or the physiologically acceptable salts thereof, and the second preparation (B) contains, in a cosmetic carrier, (B1) hydrogen peroxide, wherein the molar ratio of all resorcinol derivatives (A1), contained in preparation (A), to all developer-type oxidation dyes (A2), contained in preparation (A) define the molar ratio (A1)/(A2) having a value of at least about 1.2;

(II) applying the ready-to-use reshaping and coloring agent to the hair;

(III) mechanically and chemically reshaping the hair;

(IV) rinsing the hair; and (V) optionally drying the hair.

11. The method according to claim 10, wherein preparing comprises the preparations (A) and (B) being mixed in a quantitative ratio (A)/(B) of from about 3:1 to about 1:3.

12. The method according to claim 10, wherein mechanically and chemically reshaping of the hair occurs at a temperature of from about 20 to about 80° C.

13. The method according to claim 10, wherein mechanically and chemically reshaping comprises straightening of the hair by combing or pulling the hair straight with a comb or brush.

14. The method according to claim 10, wherein the sequence of the steps in the method is the following: step (I), followed by step (II), followed by step (III), followed by step (IV), followed by step (V).

15. The method according to claim 10, wherein the sequence of the steps is step (I), followed by step (II), followed by step (IV), followed by step (III), followed by step (V).

16. A method comprising using an agent, prepared by mixing two separately packaged preparations (A) and (B), for reshaping and coloring human hair, wherein preparations (A) and (B) are defined according to claim 1.

* * * * *